US008932859B2

(12) United States Patent
Tsien et al.

(10) Patent No.: US 8,932,859 B2
(45) Date of Patent: Jan. 13, 2015

(54) METHODS FOR ENGINEERING POLYPEPTIDE VARIANTS VIA SOMATIC HYPERMUTATION AND POLYPEPTIDE MADE THEREBY

(75) Inventors: Roger Y. Tsien, La Jolla, CA (US); Lei Wang, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1264 days.

(21) Appl. No.: 12/124,888

(22) Filed: May 21, 2008

(65) Prior Publication Data

US 2008/0293068 A1    Nov. 27, 2008

Related U.S. Application Data

(62) Division of application No. 10/984,694, filed on Nov. 8, 2004, now Pat. No. 7,393,923.

(51) Int. Cl.
| C12N 15/09 | (2006.01) |
| C12N 15/64 | (2006.01) |
| C12P 21/02 | (2006.01) |
| C12Q 1/02  | (2006.01) |

(52) U.S. Cl.
CPC .................................. *C12P 21/02* (2013.01)
USPC ............................ 435/455; 435/69.1; 435/29

(58) Field of Classification Search
None
See application file for complete search history.

(56) References Cited

U.S. PATENT DOCUMENTS

| 5,625,048 A | 4/1997 | Tsien et al. |
| 6,723,537 B2 | 4/2004 | Peele |
| 2003/0059835 A1* | 3/2003 | Tsien et al. ............ 435/7.1 |
| 2003/0087236 A1* | 5/2003 | Sale et al. ............ 435/6 |

FOREIGN PATENT DOCUMENTS

| WO | 00/34318 | 6/2000 |
| WO | WO 03/045304 A2 | 6/2003 |

OTHER PUBLICATIONS

Gossen et al. Tight control of gene expression in mammalian cells by tetracycline-responsive promoters. Proceedings of the National Academy of Sciences, USA, vol. 89, No. 12, pp. 5547-5551, Jun. 1992.*
Fecteau et al. CD40 stimulation of human peripheral B lymphocytes: Distinct reponse from naïve and memory cells. The Journal of Immunology, vol. 171, pp. 4621-4629, Nov. 1, 2003.*
Held, P. Quantitation of Peptides and Amino Acids with a Synergy™ HT using UV Fluorescence, BioTek Application Note published online at www.biotek.com, Apr. 2003.*
Bach et al., "Hypermutation Targets a Green Fluorescent Protein-Encoding Trangene in the Presence of Immunoglobulin Enhancers," *Eur. J. Immunol.*, vol. 29, pp. 1383-1389, 1999.

Bach et al, "Increased Transcription Levels Induce Higher Mutation Rates in a Hypermutating Cell Line," *The Journal of Immunology*, vol. 166, pp. 5051-5057, 2001.
Campbell et al., "A monomeric red fluorescent protein," *PNAS*, vol. 99, No. 12, pp. 7877-7882, Jun. 11, 2002.
Fukita et al., "Somatic Hypermutation in the Heavy Chain Locus Correlates with Transcription," *Immunity*, vol. 9, pp. 105-114, 1998.
Gearhart, Patricia J., "The roots of antibody diversity," Nature, vol. 419, pp. 29-31, Sep. 5, 2002.
Goff, Stephen P., "Death by Deamination: A Novel Host Restriction System for HIV-1," *Cell Press*, vol. 114, pp. 281-283, Aug. 8, 2003.
Harris et al., "RNA Editing Enyzme APOBEC1 and Some of Its Homologs Can Act as DNA Mutators," *Molecular Cell*, vol. 10, pp. 1247-1253, Nov. 2002.
Landis et al., "High-Frequency Generation of Conditional Mutations Affecting Drosophilia Melongaster Development and Life Span," *Genetics*, vol. 158, pp. 1167-1176, Apr. 25, 2001.
Li et al., "The generation of Antibody Diversity Through Somatic Hypermutation and Class Switch Recombination," *Genes & Development*, vol., 18, pp. 1-11, 2004.
Matz, M. V., et al., "Fluorescent Proteins Form NonBioluminescent Anthozoa Species," *Nature Biotechnology*, vol. 17, No. 10, pp. 969-973, Oct. 1999.
Martin et al., "Somatic Hypermutation of the AID Transgene in B and non-B cells," *PNAS*, vol. 99, No. 19, pp. 12304-12308, Jul. 25, 2002.
Martin et al., "Activation-Induced Cytidine Deaminase Turns on Somatic Hypermutation in Hybridomas," *Nature*, vol. 415, pp. 802-805, Feb. 14, 2002.
Ormo, Mats, et al., "Crystal Structure of the *Aequorea victoria* Green Fluorescent Protein," *Science*, vol. 273, pp. 1392-1395, Sep. 6, 1996.
Pasqualucci et al., "Hypermutation of Multiple Proto-Oncogenes in B-cell Diffuse Large-Cell Lymphomas," *Nature*, vol. 412, pp. 341-346, Jul. 19, 2001.
Petersen-Mahrt et al., "Aid Mutates *E. coli* Suggesting a DNA Deamination Mechanism for Antibody Diversification," *Nature*, vol. 418, pp. 99-103, Jul. 4, 2002.
Rajewsky et al., "Evolutionary and Somatic Selection of the Antibody Repertoire in the Mouse," *Science*, vol. 238, pp. 1088-1094, Nov. 20, 1987.
Sale et al., "TdT-Accessible Breaks Are Scattered Over the Immunoglobulin V Domain in a Constitutively Hypermutating B Cell Line," *Immunity*, vol. 9, pp. 859-869, Dec. 1998.
Sale et al., Ablation of XRCC2/3 Transforms Immunoglobulin V Gene Conversion Into Somatic Hypermutation,*Nature*, vol. 412, pp. 921-1026, Aug. 30, 2001.

(Continued)

*Primary Examiner* — Jennifer Dunston

(74) *Attorney, Agent, or Firm* — Morgan, Lewis & Bockius LLP

(57) ABSTRACT

Methods using somatic hypermutation (SHM) for producing polypeptide and nucleic acid variants, and nucleic acids encoding such polypeptide variants are disclosed. Such variants may have desired properties. Also disclosed are novel polypeptides, such as improved fluorescent proteins, produced by the novel methods, and nucleic acids, vectors, and host cells comprising such vectors.

9 Claims, 10 Drawing Sheets

(56) References Cited

OTHER PUBLICATIONS

Shaner et al., "Improved Monomeric Red, Orange and Yellow Fluorescent Proteins Derived from Discosoma sp. Red Fluorescent Protein," *Nature Biotechnology*, vol. 10, pp. 1-6, Nov. 21, 2004.

Shagin et al., "GFP-like Proteins as Ubiquitous Metazoan Superfamily: Evolution of Functional Features and Structural Complexity," *Molecular Biology and Evolution*, vol. 21, No. 5, pp. 841-850, 2004.

Shen et al., "The TATA Binding Protein, c-Myc and Survivin Genes Are Not Somatically Hypermutated, while Ig and BCL6 Genes are Hypermutated in Human Memory B Cells," *International Immunology*, vol. 12, No. 7, pp. 1085-1093, Mar. 31, 2000.

Storb et al., "Somatic Hypermutation of Immunoglobulin and Non-Immunoglobulin Genes," *Phil. Trans. R. Soc. Lond.*, vol. 356, pp. 13-19, 2001.

Wang et al., "Genome-wide Somatic Hypermutation," *PNAS*, vol. 101, No. 19, pp. 7352-7356, May 11, 2004.

Wang et al., "Evolution of New Nonantibody Proteins via Iterative Somatic Hypermutation," *PNAS* vol. 101, No. 48, pp. 16745-16749, Nov. 19, 2004.

Yanushevich, Yurii G., et al. "A Strategy for the Generation of Non-Aggregating Mutants of *Anthozoa* Fluorescent Proteins," *FEBS Letters 511*, pp. 11-14, 2002.

Zan et al., "Induction of Ig Somatic Hypermutation and Class Switching in a Human Monocional IgM+IgD+B Cell Line in Vitro: Definition of the Requirements and Modalities of Hypermutation," *The Journal of Immunology*, vol. 162, No. 48, pp. 3437-3447, 1999.

Zhou, Cheng et al., "Human Activation-Induced Cytidine Deaminase is Induced by IL-4 and Negatively Regulated by CD45: Implication of CD45 as a Janus Kinase Phosphatase in Antibody Diversification," *Journal of Immunology*, vol. 170, pp. 1887-1893, 2003.

\* cited by examiner atggtgagcaagggcgaggagttcatgcgcttcaaggtgcgcatggag
ggctccgtgaacggccacagttcgagatcgagggcgagggcgagggccgcccctacgag
ggcaccagaccgccaagctgaaggtgaccaaggtggcccctgccctcgcctgga
atcctgtccctcagttcatgtacggctccaaggctacgtgaagcacccccgacatc
cccgactacttgaagtgtccttccccgaggcttcaaggctgggagcgcgtgatgaacttc
gaggacggcggcgtgtgaccgtgacccaggacctcctcccgtgcaggacggagttcatc
tacaaggtgaagttgcgccgcacccaacttccctccgacgcgccccgtaatgcagaagaag
accatgggctgggaggcctcctccgacctgatgtacccccgatgcggcgcccctgaagggc
gagatcaaagatgaggctgagctcgaaggacggccactacgacgccgaggtcagacc
acctacacatggccaagaagcgtgcagctgccgcctacaagacgacatcaagctg
gacatcacctcccacaacgagactacaccatcgtggaacagtagagcgcgccgagggc
cgccactccaccgcgctaa Round 0;    Round 10;    Round 14;    Round 23;
Round 0&23;    Round 10&23;    Round 14&23;    Round 10, 14&23;

FIG. 3A

| | QY | EC | 16 | 17 | 45 | 65 | 71 | 124 | 127 | 161 | 166 | 191 |
|---|---|---|---|---|---|---|---|---|---|---|---|---|
| | | | V | R | K | F | A | L | T | I | K | G |
| mRFP | 0.26 | 80 | V | R | K | F | A | L | T | I | K | G |
| R10F5 | 0.13 | 88 | | | | C | | V | | M | | |
| R10F6 | 0.14 | 89 | | | | C | | | | M | | |
| R10D6 | 0.15 | 86 | | | | C | G | | | M | | |
| R14H4 | 0.10 | 40 | E | | | | | | | M | | |
| R14G7 | 0.11 | 42 | E | | | | | | | M | | D |
| R14C12 | 0.11 | 40 | E | | | | | | S | M | | |
| R21E1 | 0.10 | 32 | E | | | | | V | S | M | | |
| R21E3 | 0.10 | 34 | E | | | | | V | | M | | |
| R21F1 | 0.10 | 33 | E | H | | | | V | | M | | |
| R23F2 | 0.10 | 37 | E | H | | | | V | | M | R | |
| R23H6 | 0.10 | 41 | E | R | | | | V | | M | R | |

FIG. 3B mPlum

DNA sequence:

atgGTGAGCAAGGGCGAGGAGgtcatcaaggagttcatgcgcttcaaggAgcA
catggagggctccgtgaacggccacgagttcgagatcgagggcgagggcgagg
gccgcccctacgagggcacccagaccgccaGgctgaaggtgaccaagggTggc
cccctgcccttcgcctgggacatcctgtcccctcagAtcATgtacggctccaa
ggcctacgtgaagcaccccgccgacatccccgactacttgaagctgtccttcc
ccgagggcttcaagtgggagcgcgtgatgaacttcgaggacggcggcgtggtg
accgtgacccaggactcctccctgcaggacggcgagttcatctacaaggtgaa
gGtgcgcggcaccaacttccctccgacggccccgtaatgcagaagaagacca
tgggctgggaggcctccTccgagcggatgtaccccgaggacggcgccctgaag
ggcgagatGaagatgaggctgaGgctgaaggacggcggccactacgacgcga
ggtcaagaccacctacatggccaagaagcccgtgcagctgcccggcgcctaca
agaccgacatcaagctggacatcacctcccacaacgaggactacaccatcgtg
gaacagtaCgagcgcgccgagggccgccactccaccggcgcctaa

Peptide sequence:

MVSKGEEVIKEFMRFKEHMEGSVNGHEFEIEGEGEGRPYEGTQTARLKVTKGG
PLPFAWDILSPQIMYGSKAYVKHPADIPDYLKLSFPEGFKWERVMNFEDGGVV
TVTQDSSLQDGEFIYKVKVRGTNFPSDGPVMQKKTMGWEASSERMYPEDGALK
GEMKMRLRLKDGGHYDAEVKTTYMAKKPVQLPGAYKTDIKLDITSHNEDYTIV
EQYERAEGRHSTGA-

FIG. 6 mRaspberry

DNA sequence:

atgGTGAGCAAGGGCGAGGAGgtcatcaaggagttcatgcgcttcaaggtgcg
catggagggctccgtgaacggccacgagttcgagatcgagggcgagggcgagg
gccgcccctacgagggcacccagaccgccaGgctgaaggtgaccaagggTggc
cccctgcccttcgcctgggacatcctgtccctcagtGcATgtacggctccaa
ggcctacgtgaagcaccccgccgacatccccgactacttgaagctgtccttcc
ccgagggcttcaagtgggagcgcgtgatgaacttcgaggacggcggcgtggtg
accgtgacccaggactcctccctgcaggacggcgagttcatctacaaggtgaa
gctgcgcggcaccaacttccctccgacggccccgtaatgcagaagaagacca
tgggctgggaggcctccTccgagcggatgtaccccgaggacggcgccctgaag
ggcgagatGaagatgaggctgaGgctgaaggacggcggccactacgacgcga
ggtcaagaccacctacatggccaagaagcccgtgcagctgcccggcgcctaca
agaccgacatcaagctggacatcacctcccacaacgaggactacaccatcgtg
gaacagtaCgagcgcgccgagggccgccactccaccggcgcctaa

Peptide sequence:

MVSKGEEVIKEFMRFKEHMEGSVNGHEFEIEGEGEGRPYEGTQTARLKVTKGG
PLPFAWDILSPQIMYGSKAYVKHPADIPDYLKLSFPEGFKWERVMNFEDGGVV
TVTQDSSLQDGEFIYKVKVRGTNFPSDGPVMQKKTMGWEASSERMYPEDGALK
GEMKMRLRLKDGGHYDAEVKTTYMAKKPVQLPGAYKTDIKLDITSHNEDYTIV
EQYERAEGRHSTGA-

FIG. 7 mRFP1.2

DNA sequence:

atgGTGAGCAAGGGCGAGGAGgtcatcaaggagttcatgcgcttcaaggtgcgcatg
gagggctccgtgaacggccacgagttcgagatcgagggcgagggcgagggccgcccc
tacgagggcacccagaccgccaagctgaaggtgaccaagggTggccccctgcccttc
gcctgggacatcctgtcccctcagttcATgtacggctccaaggcctacgtgaagcac
cccgccgacatccccgactacttgaagctgtccttccccgagggcttcaagtgggag
cgcgtgatgaacttcgaggacggcggcgtggtgaccgtgacccaggactcctccctg
caggacggcgagttcatctacaaggtgaagctgcgcggcaccaacttcccctccgac
ggccccgtaatgcagaagaagaccatgggctgggaggcctccTccgagcggatgtac
cccgaggacggcgccctgaagggcgagatcaagatgaggctgaagctgaaggacggc
ggccactacgacgccgaggtcaagaccacctacatggccaagaagcccgtgcagctg
cccggcgcctacaagaccgacatcaagctggacatcacctcccacaacgaggactac
accatcgtggaacagtacgagcgcgccgagggccgccactccaccggcgcctaa

Peptide sequence:

MVSKGEEVIKEFMRFKVRMEGSVNGHEFEIEGEGEGRPYEGTQTAKLKVTKGGPLPFAWD
ILSPQFMYGSKAYVKHPAPIPDYLKLSFPEGFKWERVMNFEDGGVVTVTQDSSLQDGEFI
YKVKLRGTNFPSDGPVMQKKTMGWEASSERMYPEDGALKGEIKMRLKLKDGGHYDAEVKT
TYMAKKPVQLPGAYKTDIKLDITSHNEDYTIVEQYERAEGRHSTGA-

FIG. 8

METHODS FOR ENGINEERING POLYPEPTIDE VARIANTS VIA SOMATIC HYPERMUTATION AND POLYPEPTIDE MADE THEREBY

GOVERNMENT INTERESTS

This invention was made with government support under Grant No. NS27177, awarded by the National Institutes of Health and Grant NO, DE-FG03-01ER63276, awarded by the Department of Energy. The government has certain rights in this invention.

FIELD OF THE INVENTION

The present invention relates generally to the fields of chemistry and biology, more particularly, to the fields of novel proteins and nucleic acids, methods of producing novel proteins and nucleic acids.

BACKGROUND OF THE INVENTION

In Vitro and In Vivo Mutagenesis.

Directed evolution is one of the most powerful tools for engineering proteins, especially when a significant number of mutations have to be iteratively accumulated to achieve the desired phenotype (Minshull, J. & Stemmer, W. P. C. Protein evolution by molecular breeding. *Curr. Opin. Chem. Biol.* 3, 284-290 (1999); Petrounia, I. P. & Arnold, F. H. Designed evolution of enzymatic properties. *Curr. Opin. Biotech.* 11, 330 (2000)). In vitro methods for creating genetic diversity are very powerful but laborious to apply iteratively when selection has to be done on transfected cells or organisms. In vivo mutagenesis avoids repetitive transfection and re-isolation of genes but normally randomizes the entire genome wastefully rather than focusing on the gene of interest (Greener, A., Callahan, M. & Jerpseth, B. An efficient random mutagenesis technique using an *E. coli* mutator strain. *Mol. Biotechnol.* 7, 189-95 (1997)).

Polypeptide variants may provide polypeptides having improved properties as compared to the parent polypeptides. For example, a variety of *Aequorea* GFP-related fluorescent proteins having useful excitation and emission spectra have been engineered by modifying the amino acid sequence of a native sequence GFP from *A. Victoria* (see Prasher et al., *Gene* 111:229-233, 1992; Heim et al., *Proc. Natl. Acad. Sci. USA* 91:12501-12504, 1994; U.S. Pat. No. 5,625,048; International application PCT/US95/14692, now published as PCT WO96/23810, each of which is incorporated herein by reference). However, there is need for further methods for providing polypeptide variants and for improved polypeptides, including further need for fluorescent protein variants having improved properties.

Somatic Hypermutation.

B lymphocytes (B cells) can specifically mutate immunoglobulin chains through a process called somatic hypermutation (SHM). SHM uses activation-induced cytidine deaminase (AID) and error-prone DNA repair to introduce point mutations into the rearranged V regions of immunoglobulin in a rate of $\sim 1 \times 10^{-3}$ mutations per base pair per generation, $10^6$ times higher than that in the rest of the genome (Rajewsky, K., Forster, I. & Cumano, A. Evolutionary and somatic selection of the antibody repertoire in the mouse. *Science* 238, 1088-94 (1987)).

Our understanding of SHM has been further advanced by more recent work (see, e.g., Papavasiliou, F. N. & Schatz, D. G. Somatic hypermutation of immunoglobulin genes: merging mechanisms for genetic diversity. *Cell* 109 Suppl., S35-S44 (2002); Martin, A. & Scharff, M. D. AID and mismatch repair in antibody diversification. *Nat. Rev. Immunol.* 2, 605-14 (2002); Neuberger, M. S., Harris, R. S., Di Noia, J. & Petersen-Mahrt, S. K. Immunity through DNA deamination. *Trends Biochem. Sci.* 28, 305-12 (2003); Bachl, J., Carlson, C., Gray-Schopfer, V., Dessing, M. & Olsson, C. Increased transcription levels induce higher mutation rates in a hypermutating cell line. *J. Immunol.* 166, 5051-7 (2001); Wang, C. L., Harper, R. A. & Wabl, M. Genome-wide somatic hypermutation. *Proc. Natl. Acad. Sci. U.S.A* 101, 7352-7356 (2004)). Somatic hypermutation has not been used for polypeptide mutagenesis to provide polypeptide variants or improved polypeptides.

SUMMARY

The methods discovered by the present inventors permit one to use the somatic hypermutation (SHM) process and to evolve polypeptides having desired properties. For example, using the novel methods the inventors have developed monomeric fluorescent proteins with increased photostability and the longest-wavelength emissions (e.g., 649 nm) yet observed for a red fluorescent protein. The inventors have developed methods, reagents and kits that allow proteins unrelated to immunoglobulin chains to be bred directly in mammalian cells, providing engineered polypeptide variants via somatic hypermutation. Mutation of target proteins and nucleic acids by the present methods, including mutation of completely foreign genes encoding fluorescent proteins, is effective to produce new and desirable phenotypes difficult or impossible to find by conventional mutagenesis.

The present disclosure provides methods for developing novel polypeptides such as polypeptide variants. Such methods include, for example, methods for engineering a fluorescent protein variant. A polypeptide variant may be a polypeptide having desired properties, such as, for example, a fluorescent protein variant having desired fluorescent properties. Methods for developing nucleic acids encoding novel polypeptides, e.g., polypeptide variants, are also provided.

The present invention further provides novel polypeptides and nucleic acids nucleic acids encoding them. The present invention also provides vectors and cells comprising such nucleic acids and polypeptides. For example, a polypeptide variant provided by the methods disclosed herein may be a variant or fragment of a fluorescent protein, e.g., a variant or fragment of a red fluorescent protein, such as mRFP1.2 (SEQ ID NO: 1) or of other fluorescent proteins.

A variant of mRFP1.2 (SEQ ID NO: 1) may have 80%, or 90%, or 95% or greater sequence identity with SEQ ID NO: 1, and may comprise one or more amino acid substitutions with respect to the amino acid sequence of mRFP1.2 (SEQ ID NO: 1). For example, such amino acid substitutions may be selected from amino acid substitutions at positions 16, 17, 45, 65, 71, 124, 127, 161, 166, and 191, and may include one or more substitutions selected from the substitutions V16E, R17H, K45R, F65C/I, A71G, L124V, T127S, I161M, K166R, and G191D. Such variants may include additions, such as, e.g., terminal amino acid additions, and may include deletions. In some embodiments, the polypeptide variant may be mPlum (SEQ ID NO: 3) or may be mRaspberry (SEQ ID NO: 5).

An aspect of the methods disclosed herein provides a method for engineering a variant of a target polypeptide, comprising: introducing polynucleotide message encoding a target polypeptide into a cell capable of supporting somatic hypermutation, said target polypeptide comprising a polypeptide other than an immunoglobulin chain polypeptide; whereby said message encoding said target polypeptide in said cell is mutated by somatic hypermutation effective to provide a variant of said target polypeptide. A cell capable of supporting somatic hypermutation may comprise activation-induced cytidine deaminase (AID) and may be capable of error-prone DNA repair. Cells capable of supporting somatic hypermutation include B cells, and include cells selected from the group consisting of a Ramos cell (ATCC No. CRL-1596), a chicken DT40 cell (ATCC No. CRL-2111), a BL2 cell, a BL41 cell, a CL-01 cell, and an 18-81 cell.

In embodiments of the methods disclosed herein, the polynucleotide message encoding a target polypeptide comprises a promoter. For example, a promoter may be a cytomegalovirus (CMV) promoter. The promoter may be an inducible promoter. An inducible promoter may be, for example, a doxycycline-dependent TET-ON promoter. The methods disclosed herein may include inducing a high level of expression of the target polypeptide. A high level of expression of a target polypeptide may be effected, for example, by providing doxycycline to a cell transfected with message including a doxycycline-dependent TET-ON promoter. High levels of expression of a target polypeptide are expression levels that are greater than corresponding rates of expression in the absence of inducing expression of the polypeptide. Such high level of expression may be effective to provide a high mutation rate of the message (e.g., a mutation rate greater than the corresponding rate in the absence of inducing expression of the polypeptide).

Methods disclosed herein may include determining whether a cell, or a population of cells, exhibits a desired property, and/or selecting a cell or population of cells if it exhibits a desired property, such as, for example, expression of a polypeptide variant that has a desired property. Methods of determining, and/or of selecting, a cell or population of cells, may include using a fluorescence activated cell sorter (FACS).

In embodiments, the methods disclosed herein may be applied to the selected cell and its progeny. For example, further application of the methods may be applied, e.g., iteratively, to a selected cell or population of cells expressing a desired property, and further determination and/or selection performed on the selected cell or population of cells exhibiting a desired property, or on the progeny of such cells.

Further aspects of the methods for engineering a variant of a target polypeptide disclosed herein comprise a) introducing polynucleotide message encoding a target polypeptide into at least one cell of a population of cells capable of supporting somatic hypermutation, wherein said target polypeptide comprises a polypeptide other than an immunoglobulin chain polypeptide; b) actively inducing a high level of expression of said target polypeptide in said at least one cell of said population of cells, whereby said message encoding said target polypeptide in at least one cell of said population of cells is mutated by somatic hypermutation effective to provide a variant of said target polypeptide; c) selecting a cell which expresses a variant polypeptide comprising a desired property; and d) allowing proliferation of said selected cell, or expansion of a population of selected cells, without active induction of expression of said target polypeptide, effective to provide a population of selected cells. A polynucleotide message encoding a target polypeptide may include a promoter, such as an inducible promoter, as discussed above.

Steps b) and c) may be repeated and applied to a population of selected cells that was expanded during step d). Such selecting may include, for example the use of a FACS. A target polypeptide may be, for example, a fluorescent polypeptide.

Messenger ribonucleic acid (mRNA) may be isolated from a selected cell or population of cells, e.g., by methods including amplification by reverse transcriptase-polymerase chain reaction (RT-PCR), and/or sequencing of the isolated mRNA, which sequencing may include deoxyribonucleic acid (DNA) sequencing. Methods disclosed herein may include isolating nucleic acid encoding a variant of a target polypeptide from a selected cell or selected population of cells. A polypeptide variant of a target polypeptide may be isolated from a selected cell or population of cells.

Aspects of the methods disclosed herein include methods for engineering a fluorescent protein variant having a desired fluorescence property, comprising: a) introducing a polynucleotide message encoding a fluorescent protein under the control of an inducible promoter into at least one cell of a population of cells capable of supporting SHM; b) inducing a high level of expression of said fluorescent protein, whereby said message encoding said fluorescent protein in at least one cell of said population of cells is mutated by somatic hypermutation effective to provide a variant of said target polypeptide; and c) selecting a cell expressing a fluorescent protein variant having said desired fluorescent property. Fluorescent proteins suitable for the practice of the methods include, for example, a fluorescent protein selected from a Green Fluorescent Protein (GFP), a GFP variant, a Red Fluorescent Protein (RFP), and a RFP variant. In embodiments of the methods disclosed herein, the fluorescent protein is a RFP, such as, for example, mRFP1.2 (SEQ ID NO: 1). Further aspects of the methods may include d) allowing proliferation of said selected cell, or expansion of a population of selected cells, without active induction of expression of said target polypeptide, effective to provide a population of selected cells. In yet further aspects of the methods disclosed herein, a step e) may be included, comprising repeating steps b) and c) on said population of selected cells of step d).

A method for engineering a variant of a target polypeptide disclosed herein comprises a) transfecting Ramos cells with exogenous nucleic acid encoding a target polypeptide under the control of a doxycycline-dependent TET-ON promoter; b) providing doxycycline effective to contact said transfected cells with doxycycline effective to induce a high level of expression of said target polypeptide in said Ramos cells; c) selecting Ramos cells expressing said target polypeptide; d) allowing cell proliferation in the absence of further providing of doxycycline; and e) selecting Ramos cells expressing a variant or variants of said target polypeptide. A further step comprising f) repeating steps b), c) and d) on said population of selected Ramos cells of step e) may be included. In addition, in embodiments, further steps may include isolating mRNA, performing RT-PCR, and performing DNA-sequencing on material derived from said Ramos cells effective to characterize said polypeptide variant or to provide desired quantities of said polypeptide variant.

As disclosed herein, the novel methods are effective to provide novel polypeptide variants such as, for example, a polypeptide produced from a cell or progeny of a cell that was selected from a population of cells transfected with polynucleotide encoding an exogenous polypeptide, subjected to Somatic Hypermutation, and selected for desired polypeptide properties.

For example, provided herein are red fluorescent protein variants of mRFP1.2 (SEQ ID NO: 1), wherein the amino acid sequence of said modified form of an mRFP1.2 polypeptide is at least 90% homologous, or at least 95% homologous, to mRFP1.2 (SEQ ID NO: 1) and comprises the amino acid methionine (M) at a position corresponding to position 161 of mRFP1.2 (SEQ ID NO: 1) and a variant amino acid at a position corresponding to position 65, replacing the phenylalanine (F) at position 65 of mRFP, said variants selected from cysteine (C) and isoleucine (I). Such red fluorescent protein variants may further comprise at least one further substitution selected from A71G, V16E, R17H, K45R, L124V, and K166R, and may still further comprise at least one substitution selected from T127S and G191D. For example, a novel fluorescent protein provided by methods disclosed herein may comprise the amino acid sequence SEQ ID NO: 3 (mPlum), the amino acid sequence SEQ ID NO: 5 (mRaspberry), or variants thereof, and a novel nucleotide provided by the methods disclosed herein may encode an amino acid sequence comprising SEQ ID NO: 3 (mPlum), may encode an amino acid sequence comprising SEQ ID NO: 5 (mRaspberry), or variants thereof.

In other embodiments, kits are provided that include at least one polynucleotide sequence encoding a novel fluorescent protein variant. Alternatively, or in addition, the kits can provide a novel fluorescent protein variant itself. Also provided are vectors that encode the fluorescent protein variants described or taught herein. Such vectors can encode these variants. Also provided herein are suitable expression vectors. In other embodiments or the methods and compositions disclosed herein, host cells comprising any of these vectors are provided.

The methods and kits disclosed herein are useful for engineering improvements in polypeptides, such as, e.g., improved fluorescent proteins, thereby providing variants having improved features and properties. The compounds disclosed herein may be used for imaging, tagging, and other purposes. For example, the methods disclosed herein have been used to develop fluorescent proteins based on an initial fluorescent protein sequence, having longer emission wavelengths than the original fluorescent proteins. Such far-red wavelengths are desirable for improving optical imaging in intact mammals (Ray, P., De, A., Min, J. J., Tsien, R. Y. & Gambhir, S. S. Imaging tri-fusion multimodality reporter gene expression in living subjects. *Cancer Res.* 64, 1323-1330 (2004)). Further uses and advantages will be evident from the disclosure herein.

BRIEF DESCRIPTION OF THE DRAWINGS

FIG. 3A illustrates nucleotides mutated by SHM in different rounds evolution pathway of the mutant proteins (twenty random samples were sequenced in round 0, 8 in round 10, 8 in round 14, and 12 in round 23) (SEQ ID NO:2).

FIG. 3B shows amino acid mutations, quantum yields (QY), and extinction coefficients (EC) of different mutants.

FIG. 6 provides the amino acid and DNA sequence of mPlum (SEQ ID NO: 3 and SEQ ID NO: 4).

FIG. 7 provides the amino acid and DNA sequence of mRaspberry (SEQ ID NO: 5 and SEQ ID NO: 6).

FIG. 8 provides the amino acid sequence of mRFP1.2 (SEQ ID NO: 1) and the nucleic acid sequence of mRFP1.2 (SEQ ID NO: 2).

DETAILED DESCRIPTION

Definitions

Figure 1:
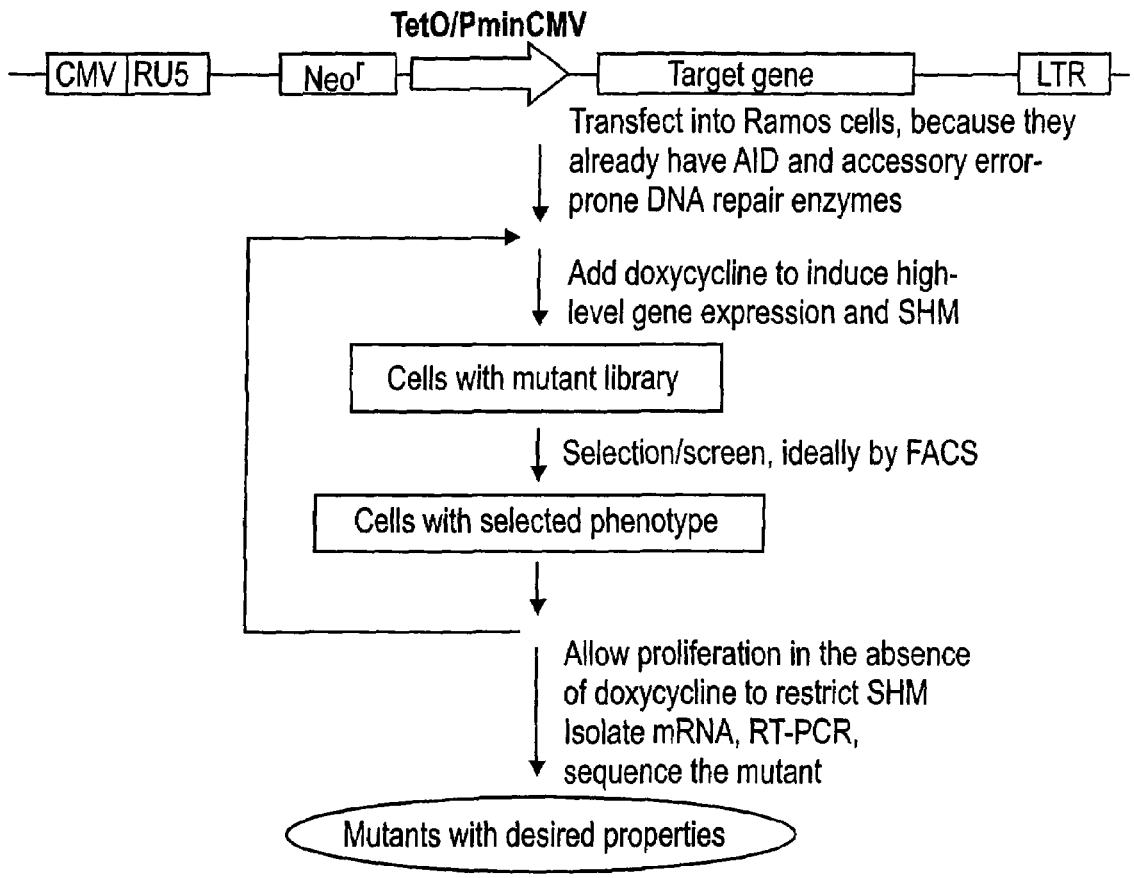
FIG. 1 illustrates a method for engineering variants of a target polypeptide (encoded by a target gene) by somatic hypermutation (SHM) in cells capable of supporting SHM (Ramos cells in this example).

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice the present invention. For purposes of the present disclosure, the following terms are defined with the following meanings, unless stated otherwise.

The terms "nucleic acid," "nucleic acid molecule," "polynucleotide," and the like refers to a deoxyribonucleotide or ribonucleotide polymer in either single-stranded or double-stranded form, and, unless specifically indicated otherwise, encompasses polynucleotides containing known analogs of native sequence nucleotides that can function in a similar manner as native sequence nucleotides. It will be understood that when a nucleic acid molecule is represented by a DNA sequence, this also includes RNA molecules having the corresponding RNA sequence in which "U" (uridine) replaces "T" (thymidine).

Reference to a nucleic acid or a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "polypeptide" or "protein" refers to a polymer of two or more amino acid residues. The terms apply to amino acid polymers in which one or more amino acid residue is an artificial chemical analogue of a corresponding native sequence amino acid, as well as to native sequence amino acid polymers. The term "recombinant protein" or "recombinant polypeptide" refers to a protein that is produced by expression of a nucleotide sequence encoding the amino acid sequence of the protein from a recombinant DNA molecule.

The term "isolated" or "purified" refers to a material that is substantially or essentially free from components that normally accompany the material in its native state in nature. Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected in significant amounts when examined using conventional methods for determining purity of such a molecule.

The term "native sequence" is used to refer to a polypeptide, nucleic acid molecule, cell, or other material that occurs in nature. For example, a polypeptide or polynucleotide sequence that is present in an organism, including in a virus. A native sequence material can be in its form as it exists in nature, and can be modified by the hand of man such that, for example, is in an isolated form.

The terms "immunoglobulin" and "immunoglobulin chain" refer to a polypeptide substantially encoded by an immunoglobulin gene or immunoglobulin genes, or antigen-binding fragments thereof, which specifically bind and recognize an analyte (antigen). Immunoglobulin chain polypeptides include antibodies and antibody fragments, and may be a polypeptide derived from an antibody or antibody fragment. For example, each of an immunoglobulin light chain, or an immunogobin heavy chain, are immunoglobulin polypeptides (see, e.g., Schultz et al., *Angew. Chem. Int. Ed. Engl.* 41:4427-4437 (2002)). The recognized immunoglobulin genes include the kappa, lambda, alpha, gamma, delta, epsilon and mu constant region genes, as well as the myriad immunoglobulin variable region genes. Antibodies exist as intact immunoglobulin chains and as well characterized antigen-binding fragments of an antibody, which can be produced by digestion with a peptidase or can using recombinant DNA methods. Such antigen-binding fragments of an antibody include, for example, Fv, Fab' and F(ab')$_2$ fragments. The term "antibody," as used herein, includes antibody fragments either produced by the modification of whole antibodies or those synthesized de novo using recombinant DNA methodologies. An immunoglobulin chain polypeptide is a polypeptide derived from an antibody or antibody fragment. For example, each of an immunoglobulin light chain, or animmunogobin heavy chain, are immunoglobulin polypeptides.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K);
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

The term "identical," when used in reference to two or more polynucleotide sequences or two or more polypeptide sequences, refers to the residues in the sequences that are the same when aligned for maximum correspondence. When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well-known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any well known algorithm (see, for example, Meyers and Miller, *Comp. Appl. Biol. Sci.* 4:11-17, 1988; Smith and Waterman, *Adv. Appl. Math.* 2:482, 1981; Needleman and Wunsch, *J. Mol. Biol.* 48:443, 1970; Pearson and Lipman, *Proc. Natl. Acad. Sci., USA* 85:2444 (1988); Higgins and Sharp, *Gene* 73:237-244, 1988; Higgins and Sharp, *CABIOS* 5:151-153; 1989; Corpet et al., *Nucl. Acids Res.*

16:10881-10890, 1988; Huang, et al., *Comp. Appl. Biol. Sci.* 8:155-165, 1992; Pearson et al., *Meth. Mol. Biol.*, 24:307-331, 1994). Alignment also can be performed by simple visual inspection and manual alignment of sequences.

Amino acid substitutions, insertions, deletions, and other changes in amino acid sequence with respect to a parent polypeptide's amino acid sequence are typically indicated by amino acid number. These and other modifications are defined herein with reference to the amino acid sequence; the first amino acid identified is the one found at the indicated location in the parent sequence, while the second indicates the substitution found in the modified form (e.g., "A71G" indicates a substitution of the amino acid alanine at position 71 in the parent sequence by glycine at the position corresponding to 71 in the variant sequence).

Where a variant amino acid sequence includes insertions or deletions, for example, the variant amino acids may be numbered to correspond to the corresponding positions along the parent amino acid sequence. Thus, for example, where a GFP variant includes an amino acid insertion following the initial methionine of the parent amino acid sequence, the inserted amino acid may be numbered 1A so that the serine in the GFP variant (the third amino acid counting from the initial methionine) is numbered 2, corresponding to serine 2 of the parent GFP.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site.

A "promoter" is an expression control sequence that regulates or affects expression (e.g., transcription or translation) of a polynucleotide operably linked to that promoter, typically by increasing the transcription or translation of the polynucleotide.

An "inducible promoter" is a promoter, the activity of which may be enhanced, activated, or otherwise increased by an external factor, agent or event. For example, a promoter whose activity may be increased by contact with a certain compound or class of compounds is an inducible promoter. Providing that compound or a compound of the class of compounds that activate the promoter acts to induce that promoter. For example, a doxycycline-dependent TET-ON promoter, whose activity is increased by contact with doxycycline, is an inducible promoter. A CMV promoter, such as the p1 promoter of Promega™, is another example of an inducible promoter (Fukita et al., *Immunity* 9: 105-114 (1998)).

The terms "actively inducing," "actively induced," "active induction," and the like, as applied to expression of a polypeptide or of nucleic acid message encoding a polypeptide, indicate an active step taken by an actor, such as a person, to induce the subject expression. For example, providing doxycyline to a cell comprising a doxycycline-dependent promoter to induce expression of message encoding a polypeptide, so as to induce expression of that polypeptide, is actively induced expression of that polypeptide. However, the constituitive expression of a polypeptide, that is not the result of addition of additional factors or of activation of an inducible promoter, is not actively induced expression.

High levels of expression of a target polypeptide are expression levels that are greater than baseline or typical levels of expression (e.g., rates of expression in the absence of actively inducing expression of the polypeptide). Such a high level of expression may be effective to provide a high mutation rate of the message (e.g., a mutation rate greater than the corresponding rate in the absence of inducing expression of the polypeptide). For example, the expression level of a polypeptide that is expressed at high levels may be 1.5, 2, 3, 5, 10 or more times than the corresponding rate of expression found in the absence of induced expression. High levels of transcription or of expression may be provided by promoters such as, e.g., a CMV promoter (Fukita et al., *Immunity* 9:105-114 (1998)).

The term "progeny" when applied to a cell includes "daughter" cells derived from a "parent" cell by cell division, whether by mitosis or meiosis, and includes other cells containing nucleic acids derived from a parent cell and introduced into the other cells by natural (e.g., conjugation or other form of gene transfer) or artificial (e.g., recombinant methods) means.

The term "variant" means a compound sharing many, often nearly all, but not all, of the chemical features of another compound (which may be termed a "parent" compound). For example, a variant of a polypeptide will have an amino acid sequence that differs in at least one amino acid from the amino acid sequence of the parent polypeptide. Similarly, a variant of a nucleic acid will have a nucleic acid sequence that differs in at least one nucleic acid from the nucleic acid sequence of the parent nucleic acid. The term "mutant" or "variant" also is used herein in reference to a fluorescent protein that contains a mutation with respect to a corresponding wild type fluorescent protein. In addition, reference is made herein to a "spectral variant" or "spectral mutant" of a fluorescent protein to indicate a mutant fluorescent protein that has different fluorescence properties with respect to the corresponding wild type fluorescent protein.

As used herein, the term "brightness," with reference to a fluorescent protein, is measured as the product of the extinction coefficient (EC) at a given wavelength and the fluorescence quantum yield (QY).

The term "determining" as used, for example, in a phrase such as, e.g., "determining whether a cell has a desired property" refers to observing, and/or measuring, and/or testing, and/or characterizing or otherwise evaluating a target (such as, e.g., a cell, or polypeptide, or nucleic acid) in order to detect whether the target exhibits or possesses as particular property, or feature, or characteristic.

The term "selecting" as used, for example, in a phrase such as, e.g., "selecting a cell that exhibits a desired property" refers to choosing, and/or segregating (e.g., separating and/or isolating) a target (such as, e.g., a cell, or polypeptide, or nucleic acid) in order to identify and/or collect those targets which exhibit or possess as particular property, or feature, or characteristic.

The term "somatic hypermutation" (SHM) refers to a process of enhanced mutation of a gene, thought to require activation-induced cytidine deaminase (AID) and error-prone DNA repair. SHM was initially described from observations of the increased mutation of immunoglobulin gene regions encoding variable regions of the light and heavy chains in B lymphocytes following antigen stimulation. AID is discussed, for example, in Smith et al., *Trends Genet.* 20:224-227 (2004).

SHM can operate on non-immunoglobulin genes provided they are being transcribed at a high enough rate (Bachl, J., Carlson, C., Gray-Schopfer, V., Dessing, M. & Olsson, C. Increased transcription levels induce higher mutation rates in a hypermutating cell line. *J. Immunol.* 166, 5051-7 (2001); Wang, C. L., Harper, R. A. & Wabl, M. Genome-wide somatic hypermutation. *Proc. Natl. Acad. Sci. U.S.A* 101, 7352-7356 (2004)).

Cells capable of supporting SHM include B cells (e.g., a bone-marrow-derived lymphocyte, or a cell of a cell-line derived from such a lymphocyte), and include such B cells as cells of the cell lines Burkitt lymphoma cell line Ramos cells (ATCC No. CRL-1596), BL2 cells and BL41 cells (Sale et al., *Immunity* 9:859-869 (1998), chicken DT40 cells (ATCC No. CRL-2111) (Sale et al., *Nature* 412:921-926 (2001), CL-01 cells (Zan et al., *J. Immunology* 162:3437-3447 (1999), and pre-B cells, such as cells of the pre-B cell line 18-81 (Bachl et al., *J Immunol* 166:5051-5057 (2001).

A polynucleotide message encoding a target polypeptide may include an inducible promoter. For example, activity of an inducible promoter may be a induced by or dependent upon a compound that may be provided, such as doxycycline, lactose, or other compound. For example, an inducible promoter suitable for the practice of the inventive methods may be a doxycycline dependent TET-ON promoter (Landis et al., *Genetics* 158: 1167-1176 (2001)). An inducible promoter provides high levels of expression of the target polypeptide (encoded by nucleic acid operatively linked to or under the influence of the promoter) under inducing conditions (e.g., in the presence of an inducing agent), yet also provides for lower expression levels if desired (e.g., at times where expansion of a population of cells may be desired with lower expression rates, lower expression rates providing lower SHM mutation rates).

In embodiments of the methods disclosed herein, a method for engineering a nucleic acid encoding a desired protein may comprise: a) introducing a polynucleotide encoding a target polypeptide into a cell capable of supporting somatic hypermutation (e.g., a cell having activation-induced cytidine deaminase (AID)) and error-prone DNA repair); b) inducing expression of mutant target protein variations; c) selecting for cells with desired property or properties; (d) optionally inducing expression of mutant target protein variations in selected cells; (e) optionally selecting for cells with desired property or properties; f) isolating desired polynucleotide produced by selected cells and/or isolating nucleic acid encoding desired target protein from selected cells; and optionally other steps.

Engineering a polypeptide may be desirable where a target property may be improved or enhanced, or where reduction or elimination of a non-desirable target property is sought. In embodiments of the methods disclosed herein, a method for engineering a method of engineering a polypeptide having desired properties may comprise: a) introducing a polynucleotide encoding a polypeptide having a detectable target property into a cell capable of supporting somatic hypermutation; b) inducing expression of mutant target polypeptides variations; c) selecting for cells having a desired property or properties based on said detectable property; (d) optionally inducing expression of mutant target protein variations in selected cells; (e) optionally selecting for cells having a desired property or properties based on said detectable property; f) isolating desired polypeptides produced by selected cells and/or isolating nucleic acid encoding desired target protein from selected cells; and optionally other steps.

A desired property may be fluorescence, which is also a detectable property. Thus, the methods disclosed herein may be used to provide a variant fluorescent protein related to a parent fluorescent protein, the variant fluorescent protein having improved properties as compared to the parent fluorescent protein. As used herein, reference to a "related fluorescent protein," to a fluorescent protein variant, or the like refers to a fluorescent protein that has a substantially identical amino acid sequence when compared to a reference fluorescent protein (e.g., a parent fluorescent protein). In general, a related fluorescent protein, when compared to the reference fluorescent protein sequence, has a contiguous sequence of at least about 150 amino acids that shares at least about 85% sequence identity with the reference fluorescent protein, and particularly has a contiguous sequence of at least about 200 amino acids that shares at least about 95% sequence identity with the reference fluorescent protein. For example an "*Aequorea*-related fluorescent protein," an "*Aequorea*-related fluorescent protein variant," a "GFP-related fluorescent protein," a "GFP variant" and the like may be exemplified by the various spectral variants and GFP mutants that have amino acid sequences that are substantially identical to *A. Victoria* GFP (see, e.g., U.S. Pat. Nos. 5,625,048; 5,777,079; 6,066,476; 6,319,669; 6,800,733, all of which are hereby incorporated by reference herein). Similarly, a "*Discosoma*-related fluorescent protein," a "*Discosoma*-related fluorescent protein variant," a "DsRed-related fluorescent related protein," a DsRed variant and the like which is exemplified by the various mutants that have amino acid sequences substantially identical to that of DsRed (see, e.g., United States Patent Application Publication Nos. 20030032088, 20030059835, and 20030170911, all of which are hereby incorporated by reference herein), and the like, for example, a *Renilla*-related fluorescent protein or a *Phialidium*-related fluorescent protein.

A useful parent fluorescent protein is the red fluorescent protein mRFP1.2 (SEQ ID NO: 1), and useful fluorescent protein variants may be variants of mRFP1.2 (SEQ ID NO: 1). In some embodiments, a useful protein variant is selected from the group of variants including mPlum (SEQ ID NO: 3) and mRaspberry (SEQ ID NO: 5).

Some of the aspects and embodiments disclosed herein may be better understood with reference to the accompanying examples, which are intended for purposes of illustration only and should not be construed as in any sense limiting the scope of the disclosure as claimed in the claims appended hereto.

EXAMPLE

The use of SHM to generate useful genetic diversity into a foreign gene is illustrated in this Example. A general scheme for the use of SHM to generate polypeptide variants is illustrated in FIG. 1. A target gene is included in a nucleic acid message also including at least one promoter (shown are CMV and TET-ON promoters). Cells capable of supporting SHM (shown here as Ramos cells) are transfected with the message, and induced to express the target gene at high levels (induction is shown here by addition of doxycycline). Induction of high levels of gene expression induces or enhances SHM. Cells are screened for a selected phenotype, such as the presence of a variant target gene product, or variants of the target gene product having desired properties, and cells meeting selection criteria are selected. Selected cells are allowed to proliferate in non-inducing conditions (shown here as the absence of doxycycline). Mutants having desired properties may be harvested at this point. Alternatively, or in addition, selected cells, including a population of selected cells after the proliferation step, may again be Subjected to induction of high levels of gene expression, as indicated by the arrow in FIG. 1 returning to the position above the phrase "Add doxycycline to induce high-level gene expression and SHM." As indicated by FIG. 1, the method may be an iterative one, allowing multiple repetitions of steps to allow for further refinement of variant gene products, or for selection of one or more gene products having multiple desired properties.

Introduction of mRFPl.2 Gene into Ramos Cells.

mRFP1.2 gene was amplified with primer LW5 (5'-CGCG-GATCCGCCACCATGGTGAGCAAGGGC-3') (SEQ ID NO:7) and LW3 (5'-CCATCGATTTAGGCGCCGGTG-GAGTGGCG-3') SEQ ID NO:8); digested with Bam HI and Cla I, and ligated into a precut pCL-NCX (Imgenex, San Diego, Calif.) derivative retroviral vector, in which the CMV promoter was replaced with the inducible TET-ON promoter. The nucleic acid sequence of mRFP1.2 is given by SEQ ID NO:2. The resultant plasmid, pCLT-mRFP, was cotransfected with pCL-Ampho (Imgenex) into 293 cells to make the retrovirus, which was subsequently used to infect Ramos cells (CRL-1596, AMERICAN TYPE CULTURE COLLECTION, ATCC, Manassas, Va.) together with another retrovirus harbouring the reverse Tet-controlled transactivator. Doxycycline (2 µglmL) was added to induce the expression of mRFP, and infected cells were sorted with FACS for 6 rounds to enrich red fluorescent cells. In the initial sort, <5% of cells became red, indicating a multiplicity of infection well below 1.

Protein Evolution and FACS Sorting.

Figure 2A:
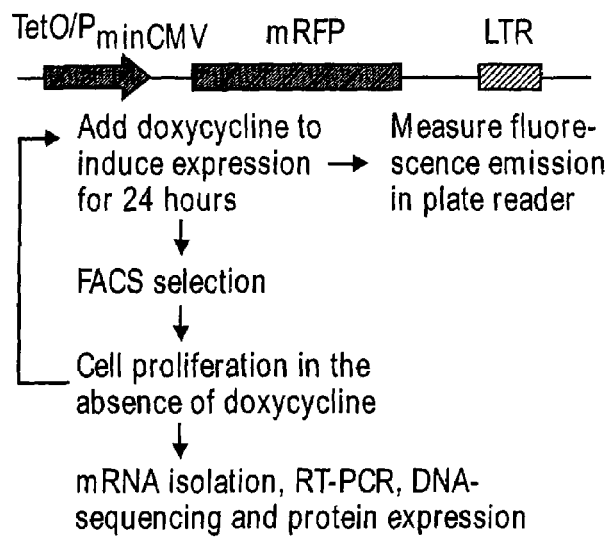
FIG. 2A illustrates the construct and evolutionary process used in a method of the invention providing directed evolution of the fluorescent protein mRFP1.2 with red-shifted emission by SHM in Ramos cells.
Figure 2B:
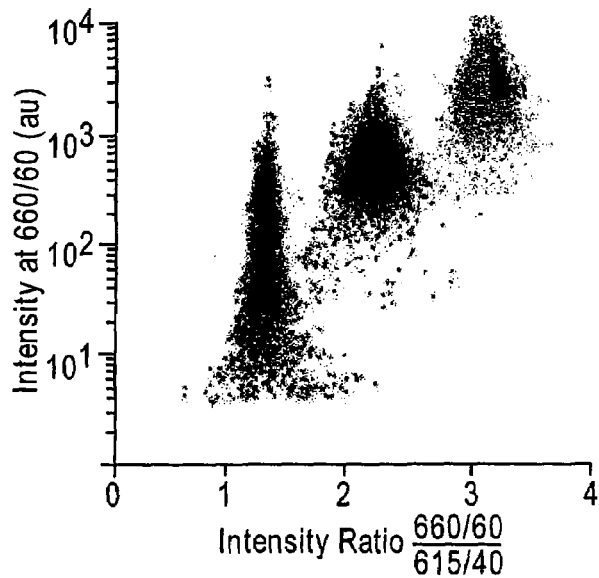
FIG. 2B illustrates typical fluorescence activated cell sorter (FACS) criteria for ratio sorting, showing cell populations of round 1, 10, and 20.

Ramos cells were grown in modified RPMI 1640 medium as suggested by ATCC. Doxycycline (2 µg/mL) was added 24 hours before FACS sorting. For ratio sorting, the cells were excited at 568 nm, and two emission filters (660/40 and 615/40) were used. The ratio of intensity at 660 nm to that at 615 nm was plotted against the intensity of 660 nm. Cells having the highest ratio and sufficient intensity at 660 nm were collected (FIG. 2B). Usually 1 million cells were collected each time, and they were grown in the absence of doxycycline until 24 hours before the next round of sorting.

Mutant Characterization.

Doxycycline (0.1 µglmL) was added to amplified cells for 10 hours. Total mRNA was extracted from these cells, and used as template for RT-PCR to clone mRFP mutant DNA with primer pCL5 (5'-AGCTCGTTTAGTGAACCGTCA-GATC 3') (SEQ ID NO:9) and pCL3 (5'-GGTCTTTCATTC-CCCCCTTTTTCTGGAG-3') (SEQ ID NO:10). These mutant mRFP genes were subcloned into a pBAD vector (Invitrogen, Carlsbad, Calif.) and expressed in E. coli. A His6 tag was added to the G-terminus to facilitate protein purification using Ni-NTA chromatography (Qiagen, Valencia, Calif.). Spectroscopic measurements were as described previously (Baird et al., Proc. Natl. Acad. Sci. 97: 11984-11989 (2000), except that concentrations of mRFPs were determined by assuming an extinction coefficient after denaturation in 0.1M NaOH of 44,000 $M^{-1} \cdot cm^{-1}$ at 452 nm, the same value as for similarly denatured Renilla GFP (Ward, W. W. in Green Fluorescent Protein: Properties, Applications, and Protocols. Chalfie, M. & Kain, S. (eds.), pp. 45-75 (John Wiley & Sons, New York, 1998); Gross, L. A., Baird, G. S., Hoffman, R. C., Baldridge, K. K. & Tsien, R. Y. The structure of the chromophore within DsRed, a red fluorescent protein from coral. Proc. Natl. Acad. Sci. U.S.A. 97, 11990-11995 (2000).

Photobleaching Measurements.

Microdroplets of aqueous protein, pH 7.4, typically 5-10 µm diameter, were created on a microscope cover slip under mineral oil and bleached using a Zeiss Axiovert 200 microscope at 14.3 $W/cm^2$ using a 75 W xenon lamp and a 540-595 nm excitation filter. Reproducible results required pre-extraction of the mineral oil with aqueous buffer shortly before microdroplet formation.

Results and Discussion.

The Burkitt lymphoma Ramos was used in the experiments described in this Example. Methods used in this Example are described in Examples 1-5 and in the present Example. Ramos is a human B-cell line that hypermutates its immunoglobulin V genes constitutively during culture Sale et al., Immunity 9:859-869 (1998) ((CRL-1596, AMERICAN TYPE CULTURE COLLECTION, ATCC, Manassas, Va.). The gene for a monomeric red fluorescent protein (mRFPl.2; SEQ ID NO: 1) Campbell et al., Proc. Natl. acad. Sci. U.S.A. 99:7877 7882 (200)) was expressed as a single copy in Ramos under the control of a doxycycline-inducible promoter, TET-ON (FIG. 2A), so that SHM could be controlled by varying the transcription level. First, fluorescent cells were enriched using 6 rounds of fluorescence activated cell sorting (FACS) of cells to which 2 µglmL of doxycycline was added to induce Mrfp expression starting 24 h before each sort. A fluorescent cell population was established with more than 96% cells fluorescent. Sequencing of different clones revealed many mutations with features of SHM scattered throughout the target gene (FIG. 3A, "round 0"). Among 20 samples sequenced, 12 of them had 1 to 3 mutations. Starting from this fluorescent population, more than 15% of cells lost fluorescence when doxycycline was added for 120 hours, whereas less than 5% lost fluorescence when doxycycline was present for only 24 hours, suggesting that more transcription generated more mutations. In control HEK293 cells lacking SHM, a similarly established fluorescent population did not change its fluorescence significantly upon such treatment.

Figure 2C:
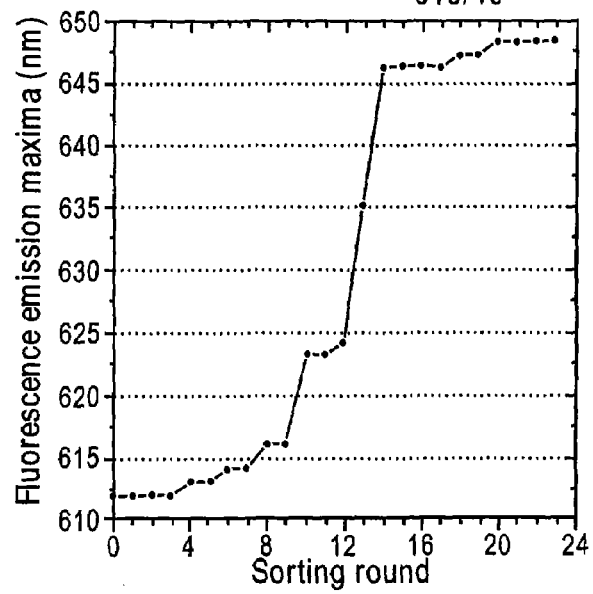
FIG. 2C illustrates fluorescence emission maxima of the Ramos cell population in each cell sorting round.

Next, whether an mRFP with red-shifted emission could be evolved directly in Ramos was tested. The parental mRFP1.2 (SEQ ID NO: 1) fluoresces with a peak at 612 nm. A longer wavelength emission would confer greater tissue penetration and spectral separation from autofluorescence and other fluorescent proteins. In each sort, a population of cells collected comprising about 5% of the population with the highest ratio of 660 nm to 615 nm emissions yet maintaining at least a minimum brightness at the former (FIG. 2B). Over 23 rounds of sorting and regrowth, the emission maxima shifted to longer wavelengths in several steps (FIG. 2C). After each major step, mutant mRFP genes were isolated, sequenced (FIG. 3A, B, C), and transferred to a standard bacterial expression system so that mutant proteins could be purified in larger quantities and characterized (FIG. 4A).

Typical fluorescence activated cell sorter (FACS) criteria for ratio sorting is illustrated in FIG. 2B, showing cell populations of round 1, 10, and 20 in blue, green, and yellow, respectively (collected cells are highlighted in red). FIG. 2C illustrates fluorescence emission maxima of the Ramos cell population in each cell sorting round. FIG. 3A illustrates nucleotides mutated by somatic hypermutation (SHM) in different rounds evolution pathway of the mutant proteins (twenty random samples were sequenced in round 0, 8 in round 10, 8 in round 14, and 12 in round 23). Amino acid mutations, quantum yields (QY), and extinction coefficients (EC) of different mutants are shown in FIG. 3B. R10F5 represents mutant F5 from round 10. We named R10D6 as "mRaspberry" and R23H6 as "mPlum". The amino acid and DNA sequences of mplum (SEQ ID NO: 3 and SEQ ID NO: 4) and of mRaspberry (SEQ ID NO: 5 and SEQ ID NO: 6) are shown in FIGS. 6 and 7, respectively.

Figure 3C:
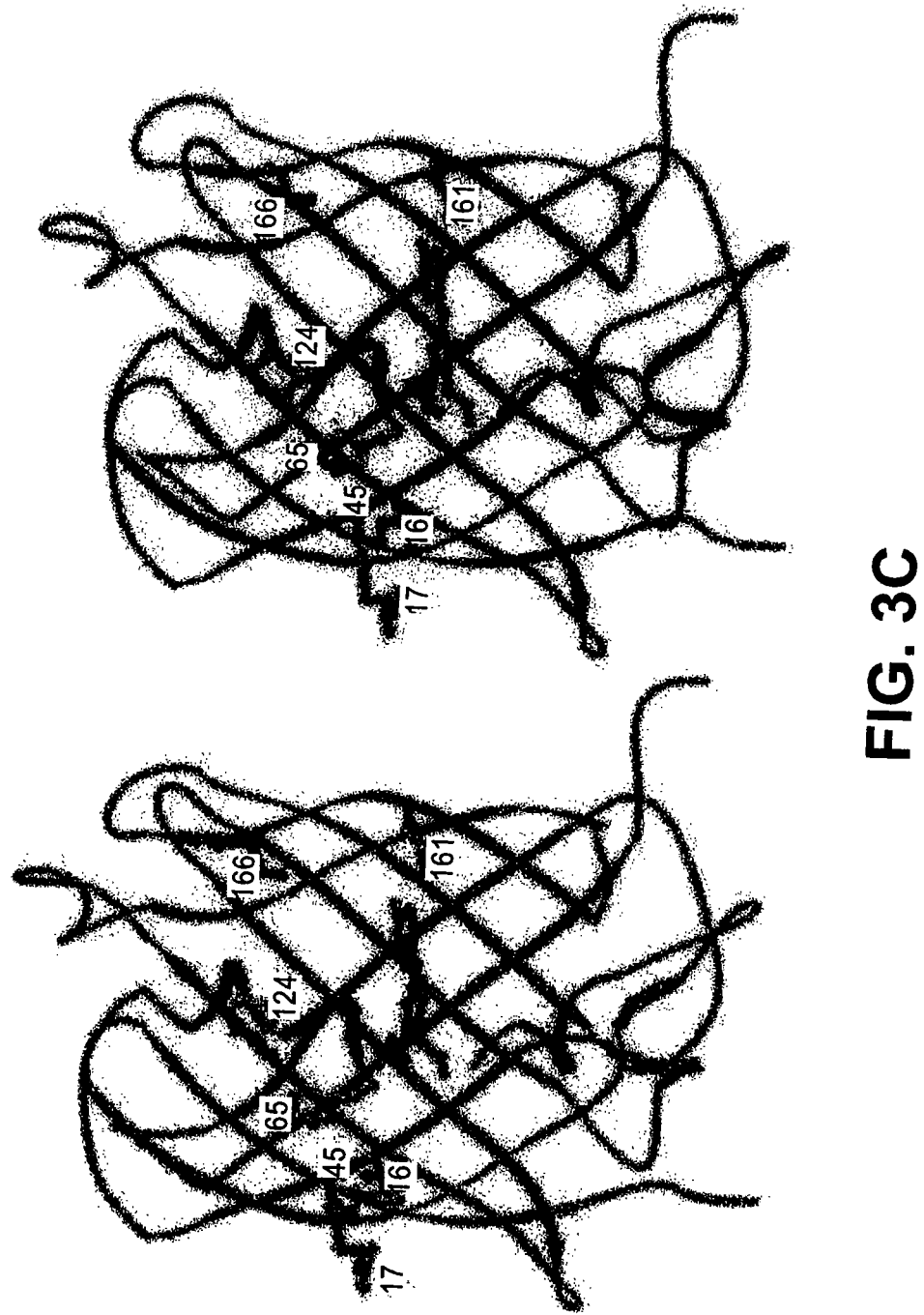
FIG. 3C illustrates a stereo view of mutation loci in mPlum based on the crystal structure of DsRed. The chromophore of RFP is shown in red. Residues are highlighted in yellow for emission-shift mutations and gray for neutral mutations.

A stereo view of mutation loci in mPlum based on the crystal structure of DsRed is shown in FIG. 3C, with the chromophore of RFP shown in red. Residues are highlighted in yellow for emission-shift mutations and gray for neutral mutations.

Figure 4A:
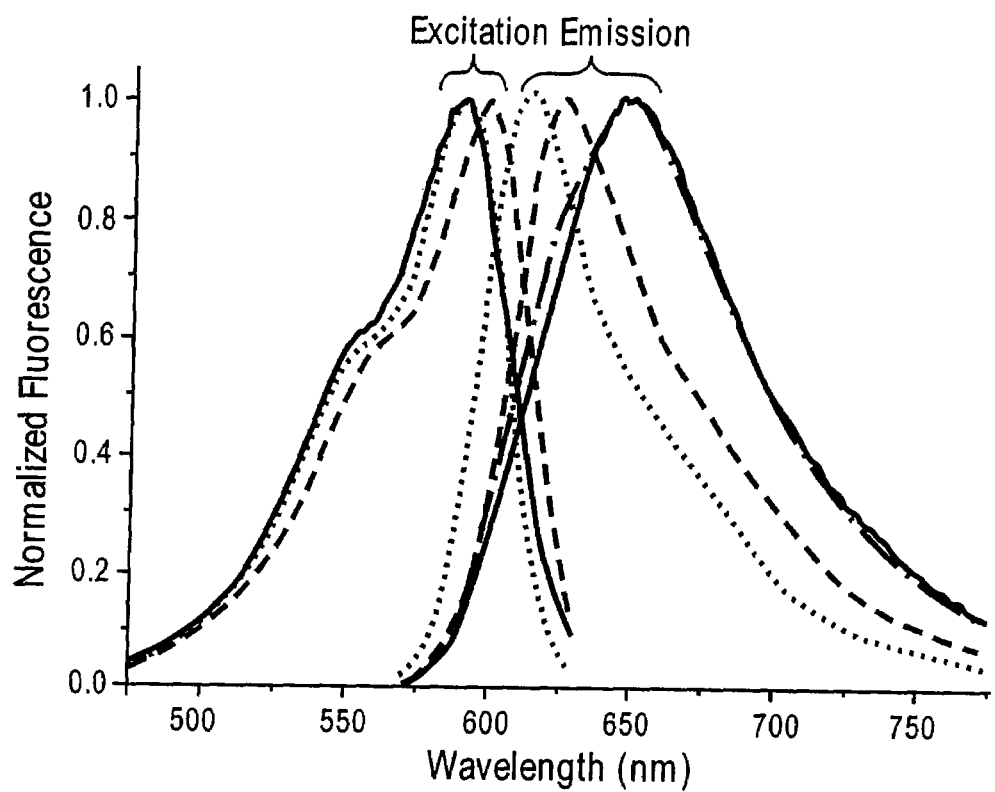
FIG. 4A illustrates the characterization of evolved mutant proteins, in which the fluorescence spectra of purified parental mRFP1.2 protein and representative mutant proteins from different rounds (dot, mRFP1.2; dash, mRaspberry; dash dot, R14H4; solid line, mPlum) are shown.
Figure 4B:
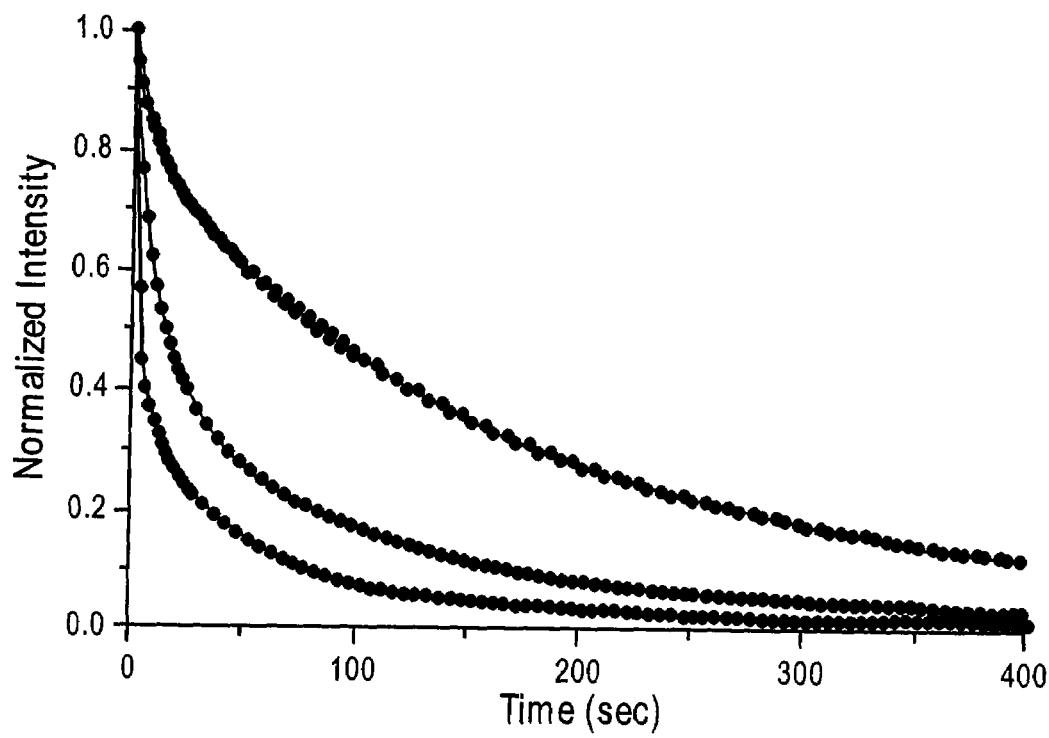
FIG. 4B shows fluorescence intensity decay during photobleaching (code is the same as in 4A).

FIG. 4A illustrates the characterization of evolved mutant proteins, in which the fluorescence spectra of purified parental mRFP1.2 protein and representative mutant proteins from different rounds (black dot, mRFP1.2; blue dash, mRaspberry; green dash dot, R14H4; red solid line, mPlum.) are shown. In round 22 and 23, brighter cells were sorted while maintaining the ratio. Thus mutants from round 21 and round 23 have similar fluorescence spectra, except that round 23 mutants have larger extinction coefficients. All emission spectra were taken at the excitation wavelength 564 nm, and emission was monitored at 640 nm for excitation spectra. Fluorescence intensity decay during photobleaching is shown in FIG. 4B (the color code is the same as in 4A).

The mutant with the longest emission wavelength (dubbed "mPlum" (SEQ ID NO: 3) in view of its monomeric nature, purplish appearance by reflected light, and deep red glow) peaked at 649 nm emission, 37 nm longer than that of the starting mRFP1.2 (SEQ ID NO: 1) and 12 nm beyond the previous furthest-red emitter, the tandem dimer t-HcRed1 (Fradkov et al., Biochem. J. 368:17-21 (2002)). The absorbance and excitation maxima of mPlum (SEQ ID NO: 3) remain at 590 nm, surprisingly unchanged from that of mRFP1.2 (SEQ ID NO: 1) and identical to that for t-HcRed1. The 59 nm Stokes' shift is unusually large. The fluorescence quantum yield of 0.10 for mPlum (SEQ ID NO: 3) is somewhat lower than the fluorescence quantum yield of 0.25 of mRFP1.2 (SEQ ID NO: 1), but still well above that of t-HcRed (0.04). The largest wavelength of excitation (598 nm), extinction coefficient (86,000 $M^{-1}cm^{-1}$) and quantum yield (0.15) were found in a round 10 mutant, "mnRaspberry" (SEQ ID NO: 5), whose emission maximum was 625 nm. Furthermore, all evolved mutants were considerably more resistant to photobleaching than the parental mRFP1.2 (SEQ ID NO: 1). When exposed to a 14.3 W/cm² beam around 568 nm light on a microscope stage, microdroplets under oil of mPlum (SEQ ID NO: 3) and mRaspberry (SEQ ID NO: 5) respectively took 80 and 14 s to bleach to 50% of initial intensity, 30- and 5.2-fold longer than mRFP1.2 (SEQ ID NO: 1) (FIG. 4B). The repeated FACS selection for cells exceeding a minimum brightness might have promoted photostability by discriminating against mutants that bleached significantly during the passage through the intense laser excitation spot.

DNA sequences of these mutants revealed the evolution pathway. Each round generated new mutations, including silent ones (FIG. 3A). Within a round, different clones share common mutations, such as F65C and I161M in round 10 (FIG. 3B). Beneficial mutations were preserved from round to round, such as I161M and V16E. Though thymine is not favored for SHM (Martin et al., Nat. Rev. Immunol. 2:605-614 (2002), it was mutated to guanine or adenine in the F65 codon to generate Cys and Ile, respectively, indicating that beneficial mutations are not limited to those most frequent in SHM. Comparison of mutations with phenotypes indicates that alterations at position 16 and 65 gave rise to the dramatic red-shift of the emission peak, whereas mutations at position 124 and 161 mainly narrowed the emission width by shrinking the short-wavelength side of the peak. The latter is a subtle beneficial effect which is usually difficult to achieve. When mapped on the crystal structure of DsRed (Yarborough et al., Proc. Natl. Acad. Sci. U.S.A. 98:462-467 (2001)) from which mRFP1.2 (SEQ ID NO: 1) was derived (FIG. 3C), residue 65 just precedes the chromophore. Residue 16 and 161 are located at the opposite ends of the chromophore with side chains facing it. Residue 124 also faces inward the helix bearing the chromophore. Mutation of these residues could directly perturb the chromophore's microenvironment resulting in emission shift. In contrast, residues 17, 45 and 166 face away the chromophore, and thus their major, contribution is to improve protein folding and brightness.

Parallel experiments using random mutagenesis or rational design based on crystal structure have not yet generated m-RFP mutants with emission maxima beyond 632 nm, suggesting that SHM can solve challenging problems in global searching. In addition, traditional in vitro saturation mutagenesis at each locus identified by SHM produced no further increase in emission wavelengths. Instead, most mutations resulted in either fluorescence loss or blue-shift. For example, the emission spectra in FIG. 5 show that SHM found the optimum substitutions at position 65 and 124. Furthermore, several residues such as T127 and K166 were mutated in some but not all SHM clones. Saturation mutagenesis at these loci indicated that they are neutral, i.e. do not affect emission wavelength (FIG. 5B). These results suggest our method is able to identify and locally optimize critical residues to cope with the selection pressure.

Figure 5A:
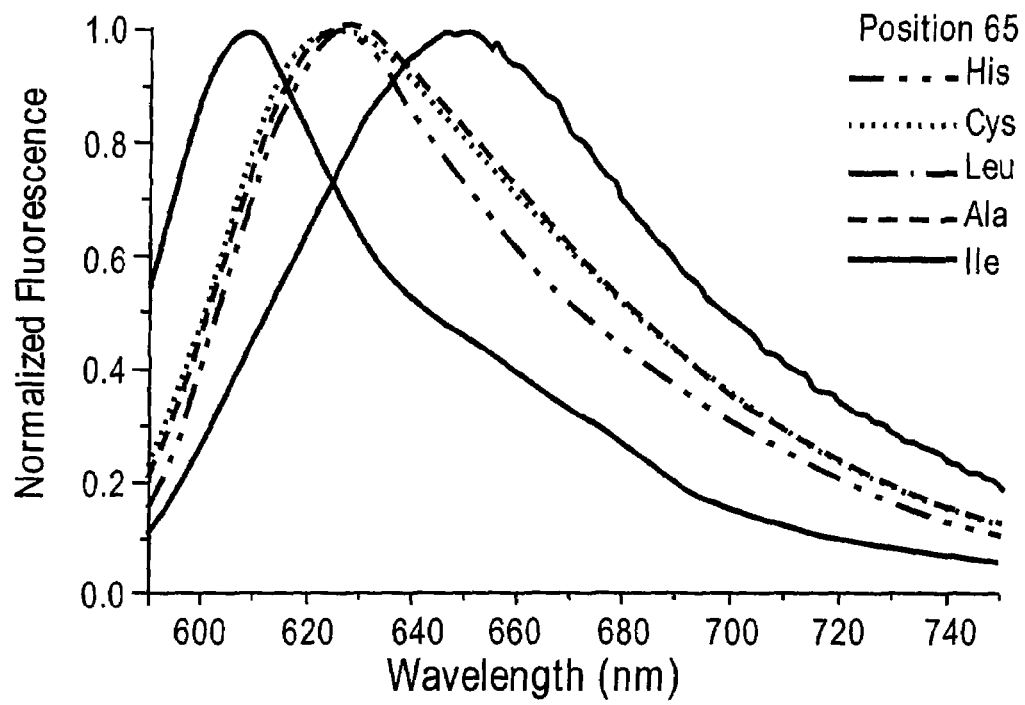
FIG. 5A shows fluorescence emission spectra of mutants with different mutations at position 65, providing a saturation mutagenesis analysis of positions identified by SHM in mPlum.
Figure 5B:
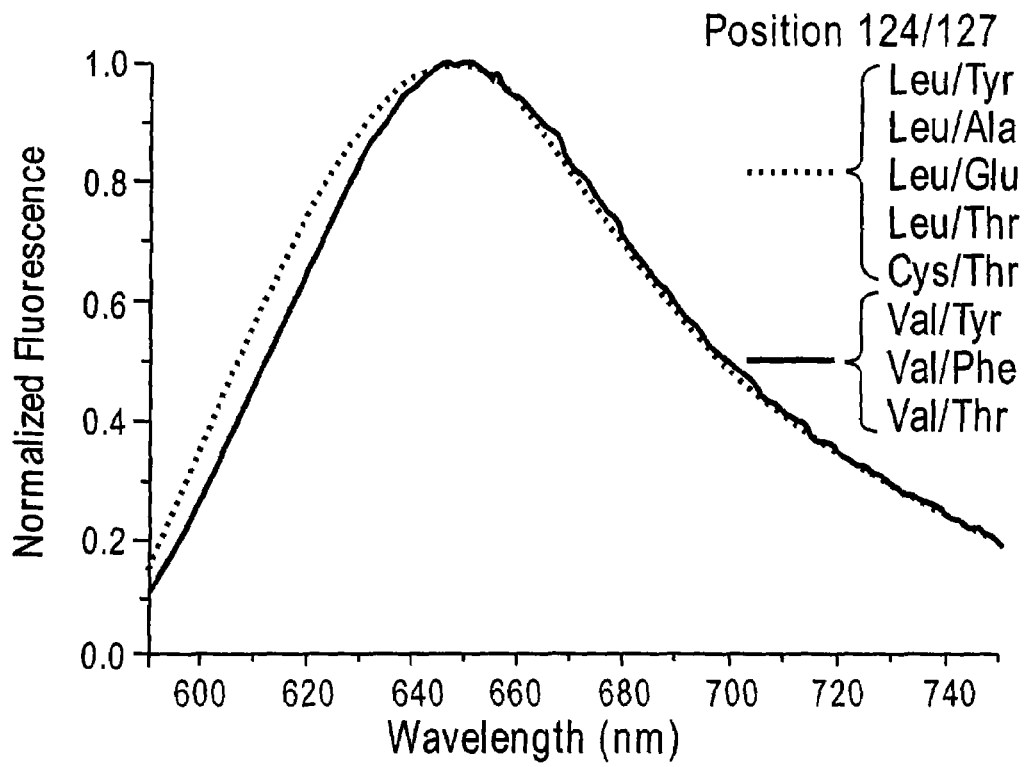
FIG. 5B shows fluorescence emission spectra of mutants with different mutations at position 124 and 127. Mutations at position 124 different from the SHM-identified Val broaden the emission peak to the short-wavelength side.

Saturation mutagenesis analysis of positions identified by SHM in mPlum is shown in FIG. 5A, showing fluorescence emission spectra of mutants with different mutations at position 65. All mutations different from the SHM-identified Ile dramatically blue-shift the emission. FIG. 5B illustrates fluorescence emission spectra of mutants with different mutations at position 124 and 127. Mutations at position 124 different from the SHM-identified Val broaden the emission peak to the short-wavelength side. Regardless of the mutations at position 127, mutants with Leu or Cys at position 124 overlap, and mutants with Val at position 124 also overlap.

SHM in vivo is believed to focus on just the V region of immunoglobulin genes. How this locus specificity is achieved is under debate (Smith et al., Trend Genet. 20:224-227 (2004)). Sequences from immunoglobulin introns and enhancers have been proposed to facilitate the targeting (Betz et al., Cell 77:239-248 (1994)). The absence of any such cis elements in our construct suggests that these elements are not required for SHM in Ramos cells. In analogous experiments, we find that a GFP from the copepod Pontellina plumata (Shagin et al., Mol. Bio. Evol. 21:841-850 (2004)) also undergoes SHM in chicken DT40 cells, a different hypermutating B-cell line (Sale et al., Nature 412:921-926 (2001)). SHM in a pre-B-cell line supplemented with AID can repair a deliberately crippled mutant of Aequorea GFP integrated anywhere in the genome remote from Ig elements (Wang et al., Proc. Natl. Acad. Sci. 101:7352-7356 (2004)). Thus three B-cell-related lines can mutate completely foreign genes encoding fluorescent proteins from three different species, in the present case producing new and desirable phenotypes difficult or impossible to find by conventional mutagenesis. Catalytic antibodies (Schultz et al., Angew. Chem. Int. Ed Engl. 41:4427-4437 (1992)) have been the showcase for using the immune system to evolve functions remote from immunology, but the repertoire of B cell creativity has now expanded outside immunoglobulins. SHM-mediated protein evolution in live cells obviates labor intensive in vitro mutagenesis and screening, samples a large protein space, and directly links genotype to cell phenotypes. An engineered error-prone DNA polymerase I can perform somewhat analogous targeted mutagenesis on multicopy colE1 plasmids in bacteria (Camps et al., Proc. Natl. Acad. Sci. 100:9727-9732 (2003)), but SHM works on single-copy integrants in well-established mammalian cell lines. SHM should provide a general strategy to evolve many other proteins, especially those whose function is best assessed in live mammalian cells.

All publications, GenBank Accession Number sequence submissions, patents and published patent applications mentioned in the above specification are herein incorporated by reference in their entirety. Various modifications and variations of the described compositions and methods will be apparent to those skilled in the art without departing from the scope and spirit of the invention. Although the invention has been described in connection with various specific embodiments, it should be understood that the invention as claimed should not be unduly limited to such specific embodiments. Indeed, various modifications of the described modes for carrying out the invention which are obvious to those skilled in protein chemistry or molecular biological arts or related fields are intended to be within the scope of the following claims.

We claim:

1. A method of engineering red fluorescent protein non wild-type variants having an altered emission peak, comprising the steps of:
   a) introducing a polynucleotide encoding the red fluorescent protein of SEQ ID NO: 1 under control of an inducible promoter into at least one cell of a population of cells which support somatic hypermutation (SHM);
   b) inducing expression of said red fluorescent protein of SEQ ID NO: 1, whereby said polynucleotide is mutated in one or more mutation rounds by SHM, wherein said mutation round provides a multiplicity of non wild-type variants of said red fluorescent protein of SEQ ID NO: 1; and
   c) selecting a cell expressing red fluorescent protein variant having an altered emission peak, as compared to the emissions peak of the red fluorescent protein of SEQ ID NO: 1, and having the sequence of SEQ ID NO: 3 or 5.

2. The method of claim 1, wherein said cells which support SHM are selected from the group consisting of Ramos cells, chicken DT40 cells, BL2 cells, BL41 cells, CL-01 cells, and 18-81 cells.

3. The method of claim 1, wherein said cells which support SHM comprise ATCC No. CRL-1596 cells.

4. The method of claim 1, wherein said inducible promoter comprises a doxycycline-dependent promoter.

5. The method of claim 4, wherein said inducible promoter is induced by the step of providing doxycycline or a suitable substitute to said cell effective to induce a high level of transcription effective to increase the mutation rate of said polynucleotide encoding said red fluorescent protein of SEQ ID NO: 1.

6. The method of claim 1, wherein said step of selecting comprises selecting using a fluorescence activated cell sorter (FACS).

7. The method of claim 1, wherein said cell which supports SHM comprises a B cell.

8. The method of claim 1, further comprising the step of isolating nucleic acid encoding the red fluorescent protein variant having the sequence of SEQ ID NO: 3 or 5 from selected cells.

9. The method of claim 8, further comprising the step of determining the sequence of the nucleic acid encoding the red fluorescent protein variant having the sequence of SEQ ID NO: 3 or 5.

* * * * *

SEQUENCE LISTING

```
<160> NUMBER OF SEQ ID NOS: 10

<210> SEQ ID NO 1
<211> LENGTH: 226
<212> TYPE: PRT
<213> ORGANISM: Artificial Sequence
<220> FEATURE:
<223> OTHER INFORMATION: Fluorescent protein (mRFP1.2)

<400> SEQUENCE: 1

Met Val Ser Lys Gly Glu Glu Val Ile Lys Glu Phe Met Arg Phe Lys
 1               5                  10                  15

Val Arg Met Glu Gly Ser Val Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Leu Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Glu Phe Ile Tyr Lys Val Lys Leu Arg Gly Thr
        115                 120                 125

Asn Phe Pro Ser Asp Gly Pro Val Met Gln Lys Lys Thr Met Gly Trp
    130                 135                 140

Glu Ala Ser Ser Glu Arg Met Tyr Pro Glu Asp Gly Ala Leu Lys Gly
145                 150                 155                 160

Glu Ile Lys Met Arg Leu Lys Leu Lys Asp Gly Gly His Tyr Asp Ala
                165                 170                 175

Glu Val Lys Thr Thr Tyr Met Ala Lys Lys Pro Val Gln Leu Pro Gly
            180                 185                 190

Ala Tyr Lys Thr Asp Ile Lys Leu Asp Ile Thr Ser His Asn Glu Asp
        195                 200                 205

Tyr Thr Ile Val Glu Gln Tyr Glu Arg Ala Glu Gly Arg His Ser Thr
    210                 215                 220

Gly Ala
225

<210> SEQ ID NO 2
<211> LENGTH: 681
<212> TYPE: DNA
<213> ORGANISM: Artificial Sequence
<220> FEATURE:
<223> OTHER INFORMATION: Nucleic acid encoding the fluorescent protein
      mRFP1.2

<400> SEQUENCE: 2
```

```
atggtgagca agggcgagga ggtcatcaag gagttcatgc gcttcaaggt gcgcatggag      60
ggctccgtga acggccacga gttcgagatc gagggcgagg cgagggccg cccctacgag      120 ggcacccaga ccgccaagct gaaggtgacc aagggtggcc ccctgccctt cgcctgggac      180
atcctgtccc ctcagttcat gtacggctcc aaggcctacg tgaagcaccc cgccgacatc      240
cccgactact tgaagctgtc cttccccgag ggcttcaagt gggagcgcgt gatgaacttc      300
gaggacggcg gcgtggtgac cgtgacccag gactcctccc tgcaggacgg cgagttcatc      360
tacaaggtga agctgcgcgg caccaacttc ccctccgacg gccccgtaat gcagaagaag      420
accatgggct gggaggcctc ctccgagcgg atgtaccccg aggacggcgc cctgaagggc      480
gagatcaaga tgaggctgaa gctgaaggac ggcggccact acgacgccga ggtcaagacc      540
acctacatgg ccaagaagcc cgtgcagctg cccggcgcct acaagaccga catcaagctg      600
gacatcacct cccacaacga ggactacacc atcgtggaac agtacgagcg cgccgagggc      660
cgccactcca ccggcgccta a                                                681

<210> SEQ ID NO 3
<211> LENGTH: 226
<212> TYPE: PRT
<213> ORGANISM: Artificial Sequence
<220> FEATURE:
<223> OTHER INFORMATION: Fluorescent protein (mPlum)

<400> SEQUENCE: 3

Met Val Ser Lys Gly Glu Glu Val Ile Lys Glu Phe Met Arg Phe Lys
1               5                   10                  15

Glu His Met Glu Gly Ser Val Asn Gly His Glu Phe Glu Ile Glu Gly
                20                  25                  30

Glu Gly Glu Gly Arg Pro Tyr Glu Gly Thr Gln Thr Ala Arg Leu Lys
            35                  40                  45

Val Thr Lys Gly Gly Pro Leu Pro Phe Ala Trp Asp Ile Leu Ser Pro
        50                  55                  60

Gln Ile Met Tyr Gly Ser Lys Ala Tyr Val Lys His Pro Ala Asp Ile
65                  70                  75                  80

Pro Asp Tyr Leu Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
                100                 105                 110

Ser Leu Gln Asp Gly Glu Phe Ile Tyr Lys Val Lys Val Arg Gly Thr
            115                 120                 125

Asn Phe Pro Ser Asp Gly Pro Val Met Gln Lys Lys Thr Met Gly Trp
        130                 135                 140

Glu Ala Ser Ser Glu Arg Met Tyr Pro Glu Asp Gly Ala Leu Lys Gly
145                 150                 155                 160

Glu Met Lys Met Arg Leu Arg Leu Lys Asp Gly Gly His Tyr Asp Ala
                165                 170                 175

Glu Val Lys Thr Thr Tyr Met Ala Lys Lys Pro Val Gln Leu Pro Gly
                180                 185                 190

Ala Tyr Lys Thr Asp Ile Lys Leu Asp Ile Thr Ser His Asn Glu Asp
            195                 200                 205

Tyr Thr Ile Val Glu Gln Tyr Glu Arg Ala Glu Gly Arg His Ser Thr
        210                 215                 220

Gly Ala
225
```

<210> SEQ ID NO 4
<211> LENGTH: 681
<212> TYPE: DNA
<213> ORGANISM: Artificial Sequence
<220> FEATURE:
<223> OTHER INFORMATION: Nucleic acid encoding the fluorescent protein (mPlum)

<400> SEQUENCE: 4

```
atggtgagca agggcgagga ggtcatcaag gagttcatgc gcttcaagga gcacatggag      60
ggctccgtga acggccacga gttcgagatc gagggcgagg gcgagggccg ccctacgag      120
ggcacccaga ccgccaggct gaaggtgacc aagggtggcc ccctgccctt cgcctgggac     180
atcctgtccc ctcagatcat gtacggctcc aaggcctacg tgaagcaccc cgccgacatc     240
cccgactact tgaagctgtc cttccccgag ggcttcaagt gggagcgcgt gatgaacttc     300
gaggacggcg gcgtggtgac cgtgacccag gactcctccc tgcaggacgg cgagttcatc     360
tacaaggtga aggtgcgcgg caccaacttc ccctccgacg gccccgtaat gcagaagaag     420
accatgggct gggaggcctc ctccgagcgg atgtaccccg aggacggcgc cctgaagggc     480
gagatgaaga tgaggctgag gctgaaggac ggcggccact acgacgccga ggtcaagacc     540
acctacatgg ccaagaagcc cgtgcagctg cccggcgcct acaagaccga catcaagctg     600
gacatcaccc tccacaacga ggactacacc atcgtggaac agtacgagcg cgccgagggc     660
cgccactcca ccggcgccta a                                               681
```

<210> SEQ ID NO 5
<211> LENGTH: 226
<212> TYPE: PRT
<213> ORGANISM: Artificial Sequence
<220> FEATURE:
<223> OTHER INFORMATION: Fluorescent protein (mRaspberry)

<400> SEQUENCE: 5

```
Met Val Ser Lys Gly Glu Glu Val Ile Lys Glu Phe Met Arg Phe Lys
  1               5                  10                  15

Val Arg Met Glu Gly Ser Val Asn Gly His Glu Phe Glu Ile Glu Gly
             20                  25                  30

Glu Gly Glu Gly Arg Pro Tyr Glu Gly Thr Gln Thr Ala Lys Leu Lys
         35                  40                  45

Val Thr Lys Gly Gly Pro Leu Pro Phe Ala Trp Asp Ile Leu Ser Pro
     50                  55                  60

Gln Cys Met Tyr Gly Ser Lys Gly Tyr Val Lys His Pro Ala Asp Ile
 65                  70                  75                  80

Pro Asp Tyr Leu Lys Leu Ser Phe Pro Glu Gly Phe Lys Trp Glu Arg
                 85                  90                  95

Val Met Asn Phe Glu Asp Gly Gly Val Val Thr Val Thr Gln Asp Ser
            100                 105                 110

Ser Leu Gln Asp Gly Glu Phe Ile Tyr Lys Val Lys Leu Arg Gly Thr
        115                 120                 125

Asn Phe Pro Ser Asp Gly Pro Val Met Gln Lys Lys Thr Met Gly Trp
    130                 135                 140

Glu Ala Ser Ser Glu Arg Met Tyr Pro Glu Asp Gly Ala Leu Lys Gly
145                 150                 155                 160

Glu Met Lys Met Arg Leu Lys Leu Lys Asp Gly Gly His Tyr Asp Ala
                165                 170                 175

Glu Val Lys Thr Thr Tyr Met Ala Lys Lys Pro Val Gln Leu Pro Gly
```

```
                180                 185                 190
Ala Tyr Lys Thr Asp Ile Lys Leu Asp Ile Thr Ser His Asn Glu Asp
        195                 200                 205

Tyr Thr Ile Val Glu Gln Tyr Glu Arg Ala Glu Gly Arg His Ser Thr
    210                 215                 220

Gly Ala
225

<210> SEQ ID NO 6
<211> LENGTH: 681
<212> TYPE: DNA
<213> ORGANISM: Artificial Sequence
<220> FEATURE:
<223> OTHER INFORMATION: Nucleic acid encoding the fluorescent protein
      (mRaspberry)

<400> SEQUENCE: 6
atggtgagca agggcgagga ggtcatcaag gagttcatgc gcttcaaggt gcgcatggag      60
ggctccgtga acgccacga gttcgagatc gagggcgagg cgagggccg ccctacgag        120 ggcacccaga ccgccaagct gaaggtgacc aagggtggcc ccctgccctt cgcctgggac     180
atcctgtccc ctcagtgcat gtacggctcc aagggctacg tgaagcaccc cgccgacatc     240
cccgactact tgaagctgtc cttccccgag ggcttcaagt gggagcgcgt gatgaacttc     300
gaggacggcg gcgtggtgac cgtgacccag gactcctccc tgcaggacgg cgagttcatc     360
tacaaggtga agctgcgcgg caccaacttc ccctccgacg gccccgtaat gcagaagaag     420
accatgggct gggaggcctc ctccgagcgg atgtaccccg aggacggcgc cctgaagggc     480
gagatgaaga tgaggctgaa gctgaaggac ggcggccact acgacgccga ggtcaagacc     540
acctacatgg ccaagaagcc cgtgcagctg cccggcgcct acaagaccga catcaagctg     600
gacatcacct cccacaacga ggactacacc atcgtggaac agtacgagcg cgccgagggc     660
cgccactcca ccggcgccta a                                               681

<210> SEQ ID NO 7
<211> LENGTH: 30
<212> TYPE: DNA
<213> ORGANISM: Artificial Sequence
<220> FEATURE:
<223> OTHER INFORMATION: Primer LW5

<400> SEQUENCE: 7
cgcggatccg ccaccatggt gagcaagggc                                      30

<210> SEQ ID NO 8
<211> LENGTH: 29
<212> TYPE: DNA
<213> ORGANISM: Artificial Sequence
<220> FEATURE:
<223> OTHER INFORMATION: Primer LW3

<400> SEQUENCE: 8
ccatcgattt aggcgccggt ggagtggcg                                       29

<210> SEQ ID NO 9
<211> LENGTH: 25
<212> TYPE: DNA
<213> ORGANISM: Artificial Sequence
<220> FEATURE:
<223> OTHER INFORMATION: Primer pCL5

<400> SEQUENCE: 9
```

```
agctcgttta gtgaaccgtc agatc                                              25

<210> SEQ ID NO 10
<211> LENGTH: 28
<212> TYPE: DNA
<213> ORGANISM: Artificial Sequence
<220> FEATURE:
<223> OTHER INFORMATION: Primer pCL3

<400> SEQUENCE: 10
ggtctttcat tcccccttt ttctggag                                            28
```